United States Patent [19]
Olsson et al.

[11] Patent Number: 5,746,732
[45] Date of Patent: May 5, 1998

[54] ABSORBENT ARTICLES

[75] Inventors: Stefan Olsson, Floda; Urban Widlund, Mölnlycke; Anders Söderbergh, Partille, all of Sweden

[73] Assignee: Molnlycke AB, Gothenburg, Sweden

[21] Appl. No.: 740,393

[22] Filed: Oct. 29, 1996

Related U.S. Application Data

[63] Continuation of Ser. No. 256,448, filed as PCT/SE93/00055, Jan. 27, 1993 published as WO93/14729, Aug. 5, 1993, abandoned.

[30] Foreign Application Priority Data

Jan. 30, 1992 [SE] Sweden ................... 9200259

[51] Int. Cl.⁶ ........................................... A61F 13/15
[52] U.S. Cl. ............................ 604/385.2; 604/385.1
[58] Field of Search ........................ 604/385.1–387, 604/397–399, 373

[56] References Cited

U.S. PATENT DOCUMENTS

| | | | |
|---|---|---|---|
| 4,738,677 | 4/1988 | Foreman | 604/385.2 |
| 4,743,246 | 5/1988 | Lawson | 604/385.2 |
| 4,808,177 | 2/1989 | DesMarais et al. | |
| 4,846,823 | 7/1989 | Enloe | |

FOREIGN PATENT DOCUMENTS

| | | |
|---|---|---|
| 0 403 832 | 12/1990 | European Pat. Off. |
| 1168903 | 7/1989 | Japan |
| 3090149 | 4/1991 | Japan |
| 3188851 | 8/1991 | Japan |
| 3218752 | 9/1991 | Japan |
| 3286760 | 12/1991 | Japan |
| 2216393 | 10/1989 | United Kingdom |

*Primary Examiner*—Debra S. Brittingham
*Assistant Examiner*—K. M. Reichle
*Attorney, Agent, or Firm*—Young & Thompson

[57] ABSTRACT

An absorbent article for one-time use only, such as a disposable diaper, incontinence guard, sanitary napkin, panty protector or the like, includes at least one hose-like fold (20, 20', 21, 21') which extends in the transverse and/or longitudinal direction of the article. Mounted in the fold (20, 20', 21, 21') are mutually spaced elastic elements (32, 32', 33, 33') which are fastened to respective end parts (27, 27', 28, 28') of the fold on respective sides of fold lines (24, 25) which depart from the upper casing layer (1) of the article, although these elastic elements (32, 32', 33, 33') are freely moveable in the intermediate part (29, 29') of the fold. The end-parts (27, 27', 28, 28') of the fold are joined to the upper casing layer (1) in a flat, permanently down-pressed state, whereas the intermediate fold part (29, 29') is forcibly lifted vertically by the action of the elastic elements (32, 32', 33, 33') as the article is fitted to the wearer and consequently curved, so as to form leakage barriers along the side edges and/or the end edges (4–7) of the article.

13 Claims, 4 Drawing Sheets

ABSORBENT ARTICLES

This application is a continuation of application Ser. No. 08/256,448, field Jul. 13, 1994, now abandoned; which is the 35 U.S.C. §317 National Stage of International Application Serial No. PCT/SE93/00055, filed Jan. 27, 1993, and which published as WO93/14729 on Aug. 5, 1993.

FIELD OF THE INVENTION

The present invention relates to a disposable absorbent article, such as a diaper, an incontinence guard, a sanitary napkin or a panty guard, comprising an absorbent pad which is embraced between a liquid-permeable upper, or inner casing layer which is intended to face towards the wearer in use, and an outer casing layer, or backing layer, which is intended to lie distal from the wearer in use, and further comprising elastication.

BACKGROUND OF THE INVENTION

The absorbent pads of such absorbent articles are intended to take-up body fluids discharged by the wearer. One problem with earlier known absorbent articles, such as diapers, is that large quantities of fluids are discharged over very short periods of time and that these large fluid quantities are unable to penetrate the liquid-permeable casing layer quickly enough. Another problem is that excrement is often not able to penetrate through the casing layer at all, unless special measures are taken to this effect. As a result, excrement, and at times also urine, remains in a receiving zone on top of the diaper, between the inner casing layer and the user, which can naturally lead to a number of problems and cause discomfort to the wearer. This liquid and excrement, particularly loose excrement, will float uncontrollably on top of the inner casing layer and travel along the simplest route under the influence of gravity, and sooner or later the liquid or the loose excrement will run out over the edges of the diaper, therewith soiling the clothes or bed linen of the wearer, to the great disadvantage of both the wearer, parents or nursing personnel. The liquid and/or excrement is able to escape at the end edges and side edges of the diaper, depending on the position of the wearer's body at the time, although such leakage, or seepage, will take place primarily at the side-edges of the diaper. That part of the diaper which lies between the wearer's thighs, the so-called crotch part, is particularly restricted laterally, and consequently the urine and excrement has only a very short distance to travel to the side edges of the diaper. It will be understood that the risk of leakage from the diaper edges is particularly great when the wearer lies on his/her side and large quantities of urine or loose excrement are discharged suddenly. Edge leakage is also a problem in articles which are intended to absorb menstruation fluid, such as sanitary napkins, since such articles are very narrow, so that they can be worn discretely and comfortably. It is known to guard against discomfort caused by this type of edge leakage, by mounting elongated elastic devices, in the form of elastic threads, bands or the like, in readily flexible side flaps provided externally of the side edges of the absorbent pad, so that the side flaps will conform sealingly to the wearer's thighs. See for instance Swedish Patent Specification 7905765-9 and European Patent Application EP 0 091 412. The side flaps are often comprised of parts of the casing layer and extend, at least laterally, beyond the edges of the absorbent pad, where they are mutually joined.

It is also known from British Patent Specification 2,161,059 A to arrange narrow folds in the inner casing layer nearest the wearer. The folds are formed in the casing layer and depart from a longitudinally extending base line, wherein the mutually opposing sidewalls of the fold are mutually joined along the full length of the fold. Mounted within the fold are elastic devices which are intended to elevate the folds, up and away from the surface of the casing layer. The two end parts of the fold, at respective end parts of the diaper, are folded laterally inwards towards the center of the diaper and there secured to the casing layer. EP 0 311 333 A2 teaches a "floating" region of a casing layer at respective side edges of a diaper, this region being delimited laterally by two joins, an outer and an inner join, between which the casing layer is unattached to the material located beneath the casing layer. These joins are mutually spaced, so that the "floating" region will have a given width. Disposed in this "floating" region is an elastic device whose ends are attached to the casing layer, while the intermediate part of said device is free from at least the underlying layer, thereby enabling the elastic device to "float" freely in said "floating" region and, at the same time, lift the casing layer within said region.

GB 2,216,393 A teaches a diaper which has barrier flaps that extend along the side edges of the diaper. The barrier flaps have a main part which extends up from the diaper, an inner crotch part which extends from said main part in towards the diaper, and an outer crotch part which extends from said main part away from the diaper. Both of the crotch parts include elastic elements which ensure that said parts will seal elastically against the wearer. In the case of the illustrated embodiment, the main part of the barrier flaps is comprised of at least two mutually abutting layers. Each of the crotch parts branches in a respective direction at the uppermost part of the main barrier part, therewith imparting a T-shape or Y-shape to the barrier flaps. It is intended that the elastication shall lie against the inside of the wearer's thighs instead of chaffing the wearer's crotch. These narrow folds, or "floating" regions of the casing layer are, however, encumbered with drawbacks. For instance, a narrow fold configured in accordance with GB 2,161,059 can be readily deflected laterally and flattened against the casing layer, so that the fold will no longer assist in protecting against leakage, therewith allowing liquid to run over the flattened fold. Because the two end parts of the fold are folded laterally and inwardly, the elastic elements will always be located laterally inwards of the base line of the fold, therewith impairing the elastic sealing effect of the fold. In practice, the tension required in the elastic elements to enable said elements to raise the fold vertically from its position on one side of the base line is so great as to render it particularly uncomfortable to the wearer. On the other hand, less tension or stretch in the elastic elements would result in a significant risk of gaps appearing between the folds and the wearer's skin, since the tension would not then be sufficient to lift the fold from its horizontal starting position. The space between the folds is also limited, because the folds are both oriented in a direction inwardly of the diaper, thereby enabling urine or excrement to collect outside the folds instead of inwardly thereof. For reasons of a trigonometrical nature, the "floating" region where the joins are spaced from one another, as described in EP 0 311 333, does not obtain a sufficiently high height and does not therefore provide a sufficiently effective barrier against leakage within the crotch area, where the risk of leakage is particularly great and where the highest possible and most stable leakage barrier is desired.

Thus, there is a need for improved protection against edge leakage in absorbent articles such as diapers, incontinence guards and sanitary napkins.

SUMMARY OF THE INVENTION

In accordance with the invention, an absorbent article of the kind defined in the introduction is characterized in that the article includes on both sides of a central receiving zone, a hose-like fold which is comprised of a pliable or flexible material layer which extends in the longitudinal direction of the article on that side thereof which is intended to face the wearer in use, such as to form leakage barriers; in that each fold has a first and a second end part and an intermediate part, two first fold lines from which the fold departs and which extend in the longitudinal direction of said fold, said first fold lines being close to one another and coinciding essentially with a common base line; in that the fold extends laterally outwards away from the base line in both directions; in that two elastic elements, such as elastic threads, bands or the like, are mounted within the hose-like fold in a pre-stretched state and along said fold, one element on each side of the base line; in that the two end parts of the fold are planar and have a maximum lateral extension and are terminated at second fold lines on each side of said base line, wherein respective elastic elements extend along said second fold lines; in that said end parts of the fold are joined to the liquid-permeable upper casing layer in a flat, permanently down-pressed state; in that the elastic elements are joined to the fold along said second fold lines at the end parts of the fold; in that the intermediate part of the fold and the elastic elements extending therethrough are freely moveable whereby in the extended, flat state of the article, the hose-like fold is flat, including also the intermediate part of said fold, with each of the two elastic elements located on a respective side of the base line, and whereby, when the article is placed on the user and therewith forcibly curved to conform to the wearer's body, the intermediate part of the fold will lift vertically as a result of the action of the elastic elements, so as to form said leakage barriers.

In another embodiment of the invention, the hose-like folds are disposed in the transverse direction of the article, preferably close to respective end edges of the article.

In one preferred embodiment of the invention, two elastic elements are mounted within a longitudinally extending fold in mutually spaced relationship, wherein the distance between said elements is equal to the width of the fold at its respective end part. The elastic elements are attached to the pliable material layer at respective end parts of the fold, these end parts, in turn, being attached to the casing layer so as to maintain the spacing of said elements at their respective end parts. When the diaper is curved in use to a generally U-shape, as seen from one side of the diaper, the elastic elements will successively approach one another in a direction from respective end parts to a region approximately central between the end parts, where the elastic elements may even coincide. The fold also narrows successively in the same direction, while, at the same time, progressively lifting vertically, away from the surface of the casing layer, and has its narrowest and its highest part in the same region, approximately centrally of the end parts, as those regions in which the elastic elements lie closest together or coincide. Thus, the fold has its greatest height approximately centrally of its two end parts, which in the case of a fold disposed along the side edges of the diaper lies in the crotch part of the diaper where the need for the highest possible barrier is greatest. This height is essentially equal to the width of the end parts of the fold where the elastic elements coincide. The high narrow fold widens successively from this region towards the end parts of the fold, since the elastic elements strive to separate laterally, one from the other, while the height of the fold decreases successively at the same time. Because the end parts of the elastic elements are attached at some considerable distance apart and on respective sides of the base line, the fold will obtain considerable resistance to lateral deformation. One important advantage afforded by the inventive construction is that the barrier will lift vertically along substantially the whole of its length as the article is curved while fitting the same to the wearer, which is not always the case with earlier known constructions. Another advantage is that because the fold is relatively wide over a comparatively large part of its length, the fold will lie softly and comfortably against the skin of the wearer. The use of more than one elastic element also enables the elements to be tensioned to a lesser extent than when only one element is used, which is beneficial from the aspect of wearer comfort. It will be understood that more than two elastic elements can be mounted within the tunnel fold, wherein the distance between the two outermost elements is equal to the width of the fold at the end part thereof. The provision of several elastic elements also greatly increases the degree of wearer comfort.

An essential feature of the invention is that the sidewalls of the fold are not connected with one another and that the elastic elements are solely connected to the end parts of the fold and to no other part thereof. One reason for this is that binding agents tend to impart stiffness and hardness to the fold and therewith possibly causing discomfort to the wearer. In unfavourable cases, the binder may also penetrate the fold material and bond the fold to the casing layer, thereby preventing the fold from lifting in the manner intended.

Another reason is because an "airy" fold and a fold that can breathe is desired, so as to enhance wearer comfort. The presence of an air-filled tunnel between the inner and the outer sidewalls of the fold enables the outer sidewall to function as a leakage barrier independently of the inner sidewall. Thus, liquid is forced to pass the inner sidewall and the corridor between said sidewalls before reaching the outer sidewall.

The end parts of the fold extend laterally both inwardly of and outwardly of the base line, and one elastic element is attached outwardly of the base line and the other element inwardly thereof. By arranging parts of the fold and an inner elastic element inwardly of the base line at the front and the rear parts of the article, there is obtained in the intermediate part of the fold a kind of collecting pocket or channel between the casing layer and the inner sidewall of the fold. This pocket is oriented inwardly of the diaper and extends in the longitudinal direction of the fold, to the region located generally centrally between the end parts of the fold, where the fold is narrowest and highest.

Furthermore, advantages are obtained by disposing parts of the fold and an outer elastic element outwardly of the base line at the front and the rear parts of the article respectively. For instance, the distance between the folds arranged at respective side edges of the article is larger than when the whole of the fold extends inwardly of the base line. This latter case would greatly restrict the urine-receiving and excrement-receiving surface between the two folds. In this context, the outer elastic element functions as a counterbalance to the inner elastic element, which strives to move the fold inwardly of the article from its attachment part inwardly of the base line, whereas the outer elastic element strives to move the fold in the opposite direction from its attachment part outwardly of the base line. Thus, the two elastic elements coact to give the fold its shape, which varies from a wide, low fold at the front and the rear parts of the article to a successively narrower and higher fold, the closer the fold approaches the center point between the two end parts of the fold. Seen from above, the fold describes a longitudinally extended X, i.e. the side edges of the fold are arcuate and curve in opposite directions towards each other.

When the two attachment parts of the two elastic elements are spaced equidistant from the common base line at the end parts of the fold and on opposite sides of the base line, the elastic sealing effect of the fold against the skin of the wearer will act in a vertical direction relative to the plane of the casing layer and immediately above the common base line, where the fold has a zero angle of inclination. As a result, the fold will move resiliently vertically up or down, depending on whether the wearer increases or decreases the pressure exerted on the fold. When the wearer causes the pressure on the fold to increase, the fold will be compressed slightly while widening at the same time, such as to obtain a generally triangular shape, with the base of the triangle facing upwards. The fold is therefore not deformed in any disadvantageous manner, and contact with the wearer's skin will be maintained during this downward movement of the fold. When the pressure exerted by the wearer decreases, the fold moves resiliently upwards while narrowing at the same time and therewith increasing the height of the fold, so as to maintain abutment with the skin and also fulfilling its function as a leakage barrier.

Although it is preferred to attach equally large end parts of the fold both inwardly and outwardly of the common base line, so as to able to obtain a maximum fold height and a favourable resilient sealing effect immediately above the common base line, it is conceivable to displace the end parts of the fold laterally in relation to the base line. In the case of folds which are disposed along the end edges of an article, it may be beneficial, for instance, when greater parts of the fold extend inwardly of the base line than outwardly thereof, so as to obtain the largest possible pocket. The requirement of sufficient distance between the folds is, after all, satisfied in that articles such as diapers are often elongated and in that the end edges of the article are therewith located at a safe distance from one another. In the case of articles in which the folds are provided along the side edges thereof, it may be advantageous, for instance, to permit the end part of the fold in the front part of the article to extend laterally with parts of different sizes inwardly and outwardly of the base line, i.e. to permit different sized parts of the inner sidewall and of the outer sidewall to be attached to the casing layer, while in the rear part of the article permitting larger parts of the fold to extend outwardly of the base line than inwardly thereof, so as to create the widest possible space between the folds at said rear part of the article.

Because the fold has a hose-like form and because the intermediate part of the elastic elements located between the points at which the element is attached to respective end parts of the fold is able to move freely both laterally and vertically, the fold can be oriented in a direction suitable for the purpose intended, by displacing the fold in relation to the common base line when fastening the end part of the fold to the casing layer, without needing to change the width of the fold to any appreciable extent or to allow the base line to describe a non-linear curve. For instance, there may be provided a base line which extends totally in the longitudinal direction of the article, while displacing the end parts of the fold laterally to an appropriate extent and still obtain a fold which extends obliquely in relation to the longitudinal axis of the article, without needing to encroach on the width of the fold at said parts. This will afford a high degree of flexibility in manufacture, since articles such as diapers are produced in a large number of sizes and shapes, all of which require their particular variant of the pattern formed by two folds, for instance along respective side edges of the diaper, in order for the diapers to function effectively, both with regard to body conformity and proof against leakage. With regard to manufacture, an advantage is gained when a linear base line extends parallel with the longitudinal axis or transverse axis of the article, this arrangement being preferred, although not necessary, since the articles are produced at a very high rate of manufacture and process steps which are performed parallel with the direction of the manufacturing line are often the most suitable from a process/technical aspect. It will be understood, however, that in spite of this, it is conceivable in some instances for the base line to be angled slightly in relation to the longitudinal or transversal axis of the article, when considered appropriate. It will be also understood that inventive longitudinally and transversely extending folds can be combined, therewith providing around all edges of the article barriers which fully circumvent the liquid-and-excrement-receiving area inwardly of the folds.

BRIEF DESCRIPTION OF THE DRAWINGS

An absorbent article construction in accordance with the invention will now be described with reference to an exemplifying embodiment thereof illustrated in the accompanying drawings, in which.

DETAILED DESCRIPTION OF THE INVENTION

Figure 1:
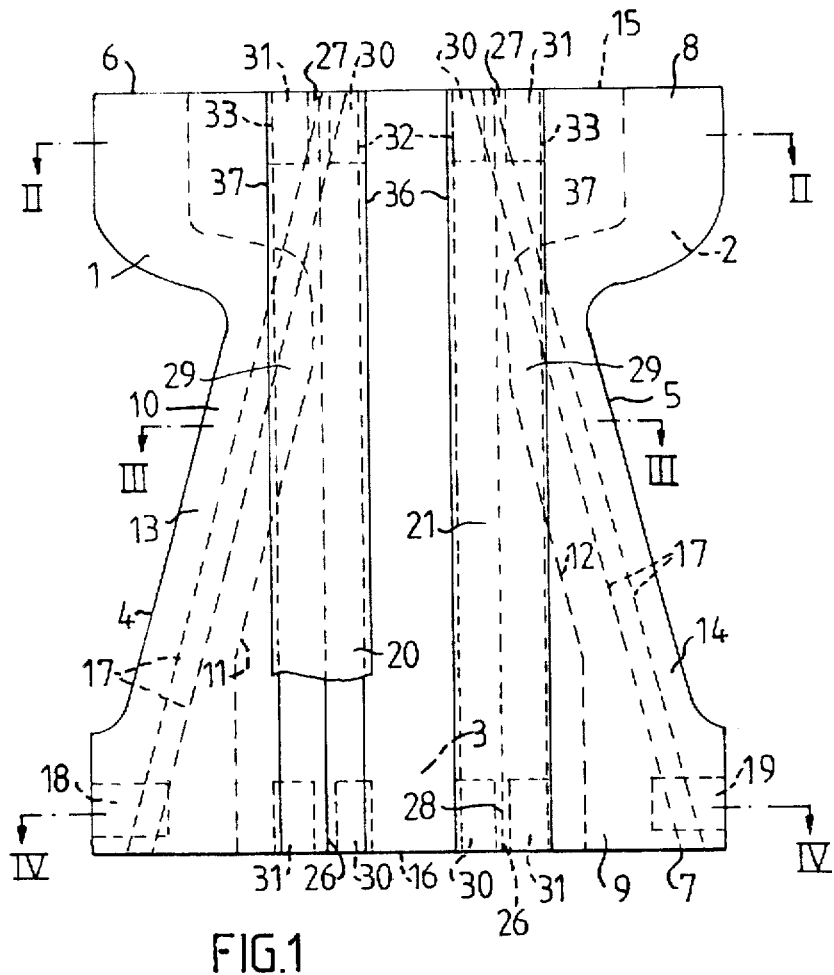
FIG. 1 illustrates a diaper from above and from that side which is intended to face towards the wearer in use, and shows the elastic elements in a stretched state, parts of one fold have been omitted from the illustration for the sake of clarity.

The diaper illustrated in FIG. 1 includes a liquid-permeable casing layer 1, a liquid-impermeable casing layer 2 and an absorbent pad 3 placed between said layers 1 and 2. The liquid-permeable casing layer 1 is placed on that side of the diaper which is proximal to the wearer in use and is comprised, for instance, of a pliable, non-woven fabric. The liquid-impermeable layer 2 is placed on the opposite side of the diaper and is comprised, for instance, of a polyethylene sheet. The absorbent pad comprises, for instance, cellulose fluff fibres or other absorbent fibres. The absorbent pad may also include so-called super-absorbents, i.e. substances whose absorbency is many times that of the substances' own weight. The super-absorbents may be comprised of polymers, such as cross-linked polyacrylates, and may be present in the form of flakes, granules, powder or fibres. The super-absorbents and the cellulose fluff fibres may be mixed together in the absorbent pad in a greater or lesser homogenous state, or the super-absorbents may, alternatively, be arranged in layers in the absorbent pad. The absorbent pad may be constructed of one or more absorbent layers which vary individually with regard to material composition, size, density, surface weight, etc. For the sake of simplicity, the absorbent pad 3 of the illustrated embodiment is shown as one single layer.

The illustrated diaper has two side edges 4, 5, two end edges 6, 7, a front part 8 which is intended to lie forwardly of the wearer in use, a back part 9 which is intended to be located rearwardly of the wearer in use, and a crotch part 10 located between the front and the back parts 8, 9 of the diaper. Both the diaper and the absorbent pad 3 have a modified T-shape, with the transverse limb of the T being located in the front part 8 of the diaper.

The two casing layers 1, 2 extend laterally beyond the side edges 11, 12 of the absorbent pad, where they are joined together to form side flaps 13, 14. The two casing layers 1, 2 are joined together at the end edges 6, 7 of the diaper without forming a corresponding end flap, by folding the liquid-impermeable layer 2 around the end edges 15, 16 of the absorbent pad 3 and slightly in over said pad and in beneath the liquid-permeable casing layer 1, in a manner not shown. The two casing layers 1, 2 are joined together in a conventional manner, for instance with the aid of an adhesive, or by heat-sealing or ultrasonic welding processes.

Elastic elements in the form of two pre-stretched elastic threads 17 are provided in respective side flaps 13, 14 extending from the back part 9 to the front part 8 of the diaper. Elastic bands, foamed material, film and like material may conceivably be used instead of elastic threads. The elastic threads 17 extend in over the absorbent pad 3 at the front part 8 of the diaper, therewith departing from the side flaps 13, 14. The elastic threads 17 in the two side flaps 13, 14 together form a V-shaped pattern, with the apex of the V located on the front part 8 of the diaper.

A pair of fastener tabs 18, 19 are provided on respective side edges 4, 5 of the back diaper part 9 in a conventional manner, these fastener tabs enabling the back diaper part 9 to be fastened to the front diaper part 8 after the diaper has been placed on the wearer.

Two folds 20, 21 in the liquid-permeable casing layer 1 are arranged along the side edges 4, 5 of the diaper. The folds have a hose-like or tubular configuration, and each has an inner sidewall 22 and an outer sidewall 23. The inner sidewall 22 faces in towards the diaper and the outer sidewall 23 faces out away from the diaper in the raised or elevated state of the fold, as will best be seen from FIG. 5.

Each inner and outer sidewall 22, 23 departs from a respective fold line 25, 24 in the liquid-permeable casing layer 1, these fold lines 24, 25 being placed so close together as to essentially coincide to form a longitudinally extending base line 26 which is common to the fold 20, 21. This common base line 26 is located inwardly of respective side edges 11, 12 of the absorbent pad and extends in a generally straight line from one end edge 6 of the diaper to the other end edge 7 thereof.

The fold 20, 21 also has two end parts 27, 28 and an intermediate part 29. The width of the fold 20, 21 is essentially equally as large at the end parts 27, 28 and the intermediate part 29. The two end parts 27, 28 are attached to the liquid-permeable casing layer 1 in lateral attachment regions 30, 31 both inwardly and outwardly of the common base line 26, and are delimited laterally by respective second fold lines 36, 37. The end parts of the fold may be bonded to the casing layer with the aid of an adhesive, or attached thereto by ultrasonic welding, heat-sealing or some other process suitable for the purpose intended.

Figures 10, 11:
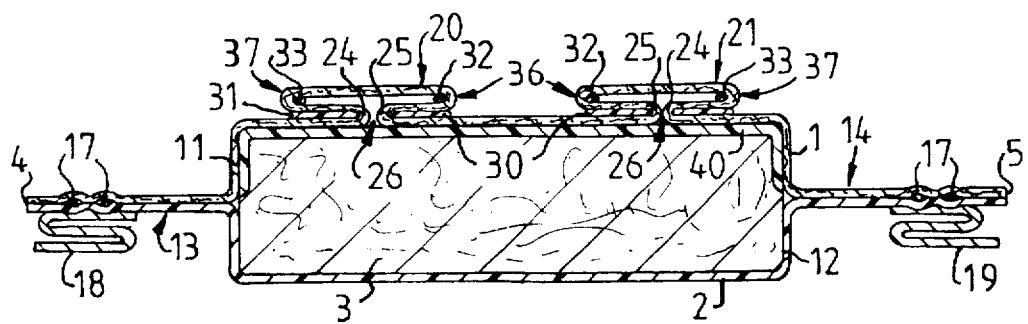
FIG. 10 is a perspective view similar to FIG. 6 of a diaper having fold which extend to different extents with respect to base line.
FIG. 11 is a cross-sectional view similar to FIG. 4 of a diaper having an additional casing layer between the upper casing layer and the absorbent pad.

Since the fold 20, 21 has the same width over the whole of its length and the common base line 26 extends in the direction of the long axis of the diaper, parts of the inner sidewall 22 and the outer sidewall 23 of the fold will be attached to the casing layer 1, the inner sidewall 22 being attached inwardly of the common base line 26 in attachment region 30 and the outer sidewall 23 being attached outwardly of the common base line 26 in attachment regions 31. The fold 20, 21 is displaced laterally, so that those fold parts which are attached outwardly of the common base line 26 will be generally the same size as those parts which are attached inwardly of said common base line. As best seen in FIG. 10, the fold 20, 21 may however extend laterally to different extent in both directions from the base line at least at one end part of the fold. However, for reasons of a process/technical nature, it is conceivable for the width of the fold 20, 21 at the end parts 27, 28 to be somewhat smaller when joining the end parts 27, 28 to the liquid-permeable casing layer 1, for instance due to unintentional crumpling or creasing of the fold sidewalls.

Two elastic elements 32, 33, for instance in the form of pre-stretched elastic threads, bands or the like, are mounted within the fold 20, 21. The elastic elements 32, 33 are attached to the end parts 27, 28 of the fold 20, 21, for instance with the aid of an adhesive, but are free to move in relation to the fold 20, 21 and in relation to each other in the intermediate part 29 of the fold. Neither are the inner and the outer sidewalls 22, 23 joined together at this intermediate part 29 of the fold. The elastic elements 32, 33 within the fold 20, 21 are also spaced apart at a distance which is equal to the width of the end part 27, 28 of the fold, i.e. at respective second fold lines 36, 37. When the diaper is extended, i.e. in the manner shown in FIG. 1, the elastic elements 32, 33 extend parallel with one another along respective second fold lines 36, 37 along the full length of respective folds 20, 21. The greater the distance between the elastic elements 32, 33 at the end parts 27, 28 of the fold, the farther the elastic elements 32, 33 are spaced from one another along the fold 20, 21 before said elements 32, 33 merge with one another and raise the fold 20, 21 to its maximum height in the crotch part 10 of the diaper when curving the diaper in order to place it around the wearer's body. This enables the fold to be stretched so as to exhibit width and stability in the front part and back part 8, 9 of the diaper. It is conceivable, of course, that because of process/technical reasons, the elastic elements 32, 33 will not be positioned exactly at the maximum distance afforded by the width of the fold, although deviations of one or two millimeters can be considered immaterial, since the fold has a width of at least two centimeters. The most important criterion is that the elastic elements are spaced at the greatest possible distance from one another.

Figure 2:
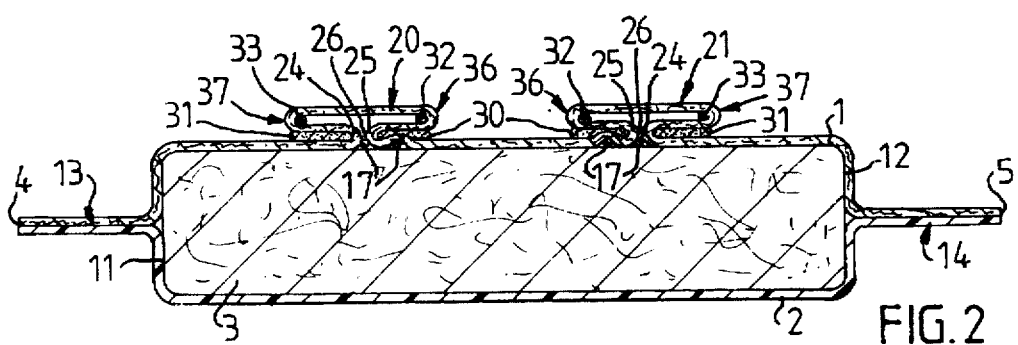
FIG. 2 is a cross-sectional view of the diaper shown in FIG. 1, taken on the line II—II.
Figure 3:
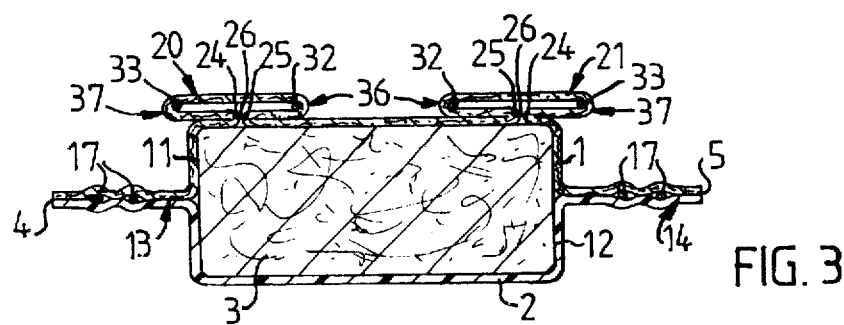
FIG. 3 is a cross-sectional view of the diaper shown in FIG. 1, taken on the line III—III.
Figure 4:
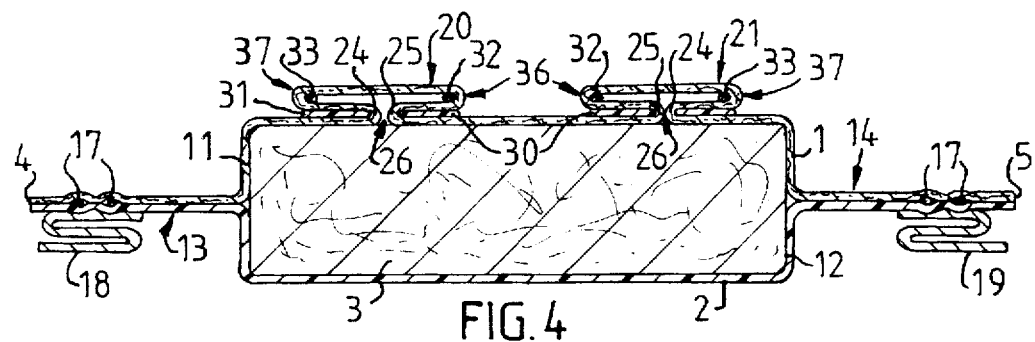
FIG. 4 is a cross-sectional view of the diaper shown in FIG. 1, taken on the line IV—IV.

FIGS. 2–4 are cross-sectional views of the diaper shown in FIG. 1 at three different positions, i.e. in the front part 8, the crotch part 10 and the back part 9 of the diaper respectively. The illustrated size ratios between the different widths, lengths and thicknesses of the illustrated structural elements may appear to be disproportionate in several instances. This is because these parameters have been either enlarged or reduced for the sake of clarity.

FIG. 2 illustrates how the two folds 20, 21 are fastened to the liquid-impermeable casing layer 1 relative to the common base line 26 in respective fastening regions 30, 31. FIG. 2 also shows the positioning of the elastic elements 32, 33 within respective end parts 27 of the fold. The elastic elements 17 extend along the side edges of the diaper and are attached inwardly of respective side edges 11, 12 of the absorbent pad in the front part 8, between said pad and the liquid-permeable casing layer 1. The elastic element 17 extend from the front part 8 of the diaper in a direction towards the back part 9 thereof and parallel with the obliquely cut parts of the diaper side edges 4, 5 in the crotch part 10, wherein the elastic element 17 from the crotch part 10 and rearwards are attached in the side flaps 13, 14, as illustrated in FIGS. 3 and 4. It will also be seen from FIG. 3 that when the elastic elements 17, 32, 33 are stretched, the folds 20, 21 will extend slightly outside respective side edges 11, 12 of the absorbent pad, since the crotch part 10 of the pad 3 is narrower at the crotch part 10 than at the front and back parts 8, 9 of the diaper. FIG. 4 shows that, in principle, the two folds 20, 21 are fastened at the back part 9 in the same manner as at the front part 8. FIG. 4 also shows fastener tabs 18, 19 attached to the outer surface of the liquid-impermeable backing layer 2, in a Z-folded configuration.

Figure 5:
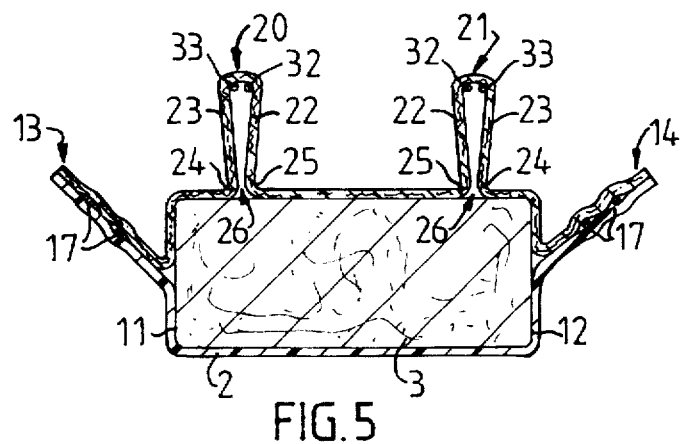
FIG. 5 is a cross-sectional view of the diaper shown in FIG. 1, taken on the line III—III, but with the elastic elements shown contracted from their stretched state.

When the elastic elements 17, 32, 33 contract from their stretched state, the two folds 20, 21 of the diaper will lift in the crotch part 10, as shown in FIG. 5. The section shown in FIG. 5 is taken at the same place as the section shown in FIG. 3. FIG. 5 shows that in this state of the diaper, the two elastic elements 32, 33 have moved together, so as not to be spaced apart in this region of the diaper and at that moment in time. Contraction of the elastic element 17 also causes the side flaps 13, 14 to be curved upwards, as will also be seen from FIG. 5.

Figure 6:
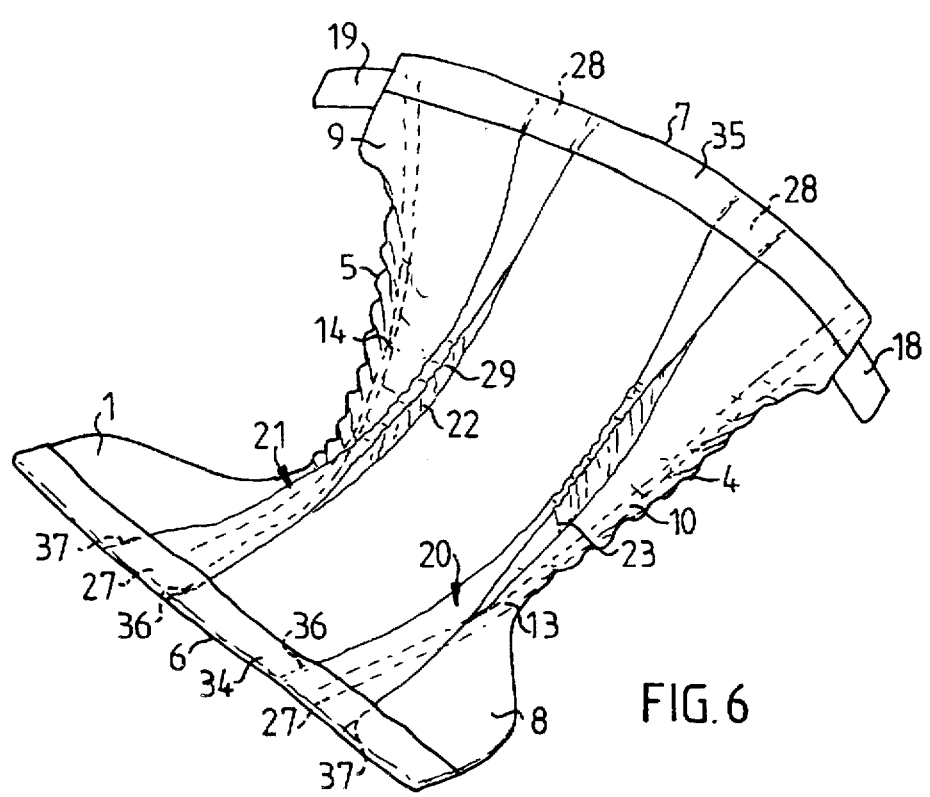
FIG. 6 is a perspective view of a diaper with the elastic elements contracted from their stretched state.

FIG. 6 is a perspective view of an inventive diaper. The manner in which the end parts 27, 28 of the folds are attached differs in the case of the diaper according to the FIG. 6 embodiment, although in other respects the diaper is identical to the diaper shown in FIG. 1.

FIG. 6 shows how the folds 20, 21 narrow down from their respective end parts 27, 28 in a direction towards the intermediate part 29, while rising vertically above the common base line 26 at the same time. A tape 34, 35 is placed along the respective end edges 6, 7 of the diaper, over the liquid-permeable casing sheet 1 and over respective end parts 27, 28 of the folds. The tape 34, 35 functions to hold the end parts 27, 28 of the folds in a flattened and extended state against the casing layer 1.

Figure 7:
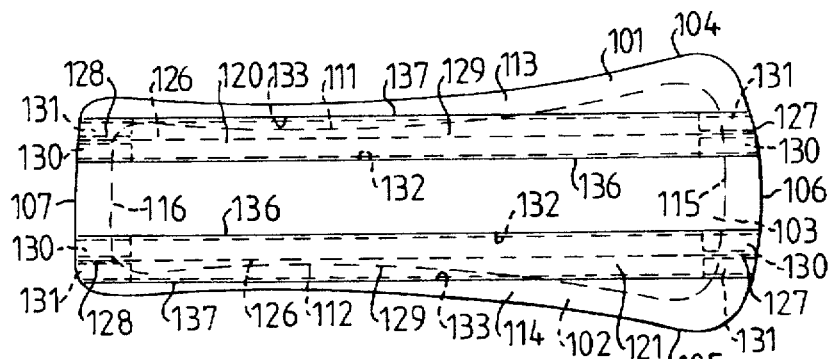
FIG. 7 shows a sanitary napkin from above, with the elastic elements in a stretched state, said view being taken from the side which is intended to face towards the wearer in use.
Figure 8:
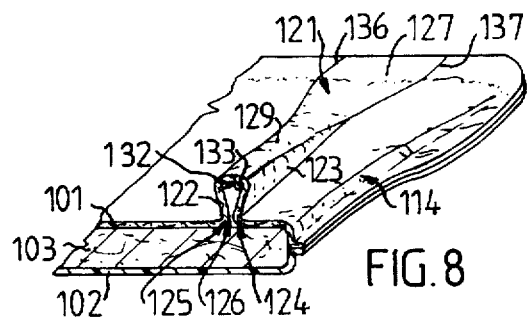
FIG. 8 is a perspective view of part of the napkin shown in FIG. 7, illustrating a section of a fold in which the elastic elements have contracted from their stretched state.

FIGS. 7–8 illustrate a sanitary napkin constructed in accordance with the invention. The illustrated sanitary napkin includes a liquid-permeable casing layer 101, a liquid-impermeable casing layer or back sheet 102, and an absorbent pad 103 placed between the two casing layers 101, 102. The liquid-permeable casing layer 101 is placed on that side of the napkin which is intended to face towards the wearer in use and is comprised, for instance, of a non-woven fabric or a perforated plastic film. The liquid-impermeable layer 102 is comprised, for instance, of a plastic film or a non-woven fabric which has been made hydrophobic. The absorbent pad 103 may comprise one or more layers of absorbent material, for instance cellulose fluff with or without admixture with superabsorbents. In FIG. 8, the absorbent pad 103 is shown to comprise only one single layer.

The illustrated napkin has two side edges 104, 105 and two end edges 106, 107. The two casing layers 101, 102 extend beyond the edges 111–112, 115–116 of the absorbent pad and are there joined together and form side flaps 113, 114. The casing layers 101, 102 are conveniently joined together with the aid of some known technique, for instance as by gluing, heat-welding or ultrasonic welding. The liquid-permeable casing layer 101 has two folds 120, 121 which extend along the side edges 104, 105 of the napkin. These folds are shown in a flat, extended state in FIG. 7. As will best be seen from FIG. 8, the folds have a tubular or hose-like configuration and when raised present an inner sidewall 122 and an outer sidewall 123. The inner sidewall 122 faces in towards the napkin and the outer sidewall 123 faces outwardly of the napkin.

Each of the inner and outer sidewalls 122, 123 extends from a respective fold line 124, 125 on the liquid-impermeable casing layer 101, these fold lines 124, 125 being located so close together as to essentially coincide to form a common, longitudinally extending fold base line 126. The common base line 126 is arranged inwardly of respective side edges 111, 112 of the absorbent pad and extends in an essentially straight line, from one end edge 106 of the napkin to the other end edge 107.

The fold 120, 121 also has two end parts 127, 128 and an intermediate part 129, and has essentially the same width at both end parts 127, 128, and in the intermediate part 129. The two end parts 127, 128 are attached to the liquid-permeable casing layer 101 in lateral attachment regions 130, 131 both inwardly and outwardly of the common base line 126 and are flattened against the casing layer 101 at said end parts 127, 128, such as to define the fold laterally by respective second fold lines 136, 137. The end parts of the fold can be secured, for instance, with the aid of an adhesive, or by an ultrasonic welding process, a heat-sealing process or by some other process suitable to this end.

Since the fold 120, 121 has the same width over the whole of its length and since the common base line 126 extends in the longitudinal direction of the napkin, parts of the inner sidewall 122 and of the outer sidewall 123 will be fastened to the casing layer 101, the inner sidewalls 122 in the attachment regions 130 inwardly of the common base line 126 and the outer sidewall 123 in the attachment regions 131 outwardly of the common base line 126. The fold 120, 121 is displaced laterally, so that those parts of the fold 120, 121 which are secured outwardly of the common base line 126 will be roughly the same size as those fold parts which are secured inwardly of the common base line 126.

Two elastic elements 132, 133, for instance pre-stretched elastic threads, bands or the like, are mounted within the fold 120, 121 in the same manner as that described with reference to the diaper illustrated in FIGS. 1–6.

FIG. 8 shows that the elastic elements 132, 133 approach each other within the fold 121, so as to coincide in a region of the intermediate fold part 129. The fold is wide and low at its end part 127, but rises and tapers off in a direction towards the intermediate part 129. The fold 121 therewith forms a high, stable, comfortable and resilient sealing barrier which effectively counteracts leakage of menstruation fluid over the side edges of the napkin.

Figure 9:
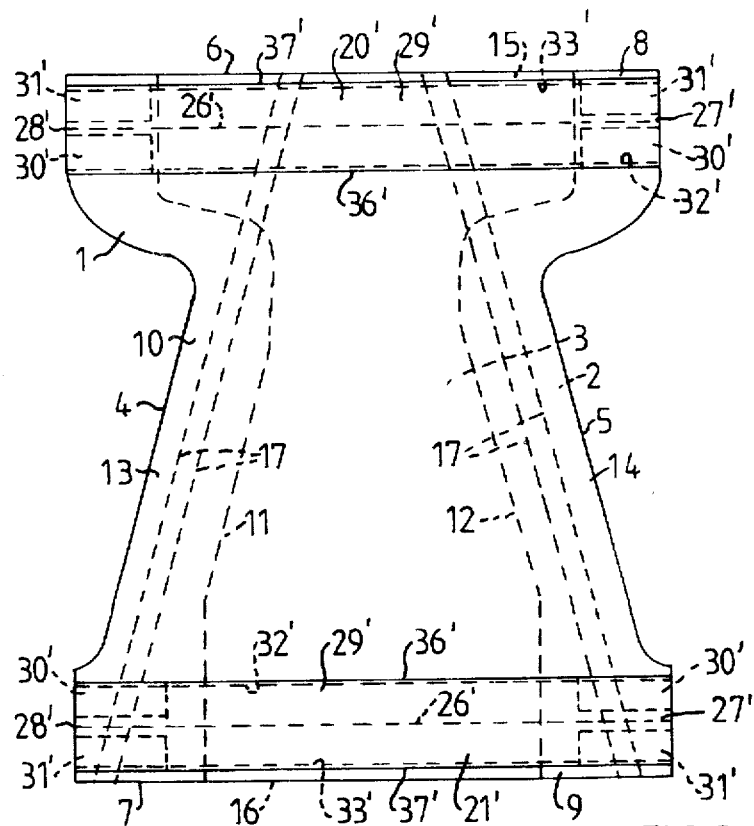
FIG. 9 illustrates from above a diaper according to another embodiment, with the elastic elements in a stretched state, said view being taken from the side which is intended to face towards the wearer in use.

FIG. 9 illustrates an embodiment of the invention in which the hose-like folds 20', 21' are arranged in the transverse direction of a diaper instead of in its longitudinal direction. The diaper shown in FIG. 9 and the folds 20', 21' are otherwise similar to the diaper and folds shown in FIG. 1. The fastener tabs shown on the diaper of the FIG. 1 embodiment and used to secure the diaper to the wearer are not shown in FIG. 9. It will be understood, however, that the diaper shown in FIG. 9 may also be provided with such fastener tabs, conveniently attached at the same positions as the fastener tabs on the diaper shown in FIG. 1.

The hose-like folds 20', 21' in FIG. 9 are identical with the folds 20, 21 shown in FIG. 1, and consequently corresponding structural elements have been identified by the same reference numeral but with the addition of an apostrophe. The hose-like folds 20', 21' of the FIG. 9 embodiment are disposed along respective end edges 6, 7 of the diaper. The folds 20', 21' are, in other respects, configured in precisely the same manner as the earlier described longitudinally extending folds 20, 21. When the diaper is fitted to a wearer, the end edges of the diaper are curved around the stomach and the backside of the wearer, wherewith the transverse folds 20', 21' will rise from their flattened, extended state, in the same way as the longitudinally extending folds 20, 21, to form a barrier against leakage along the end edges of the diaper. This diaper construction also provides a leakage barrier which seals resiliently against the body of the wearer in a vertical direction relative to the plane of the casing layer 1 and in the end parts 27', 28' of the fold, because the elastic elements 32', 33' are uniformly spaced laterally from the common base line 26' of the fold.

The invention shall not be considered to be restricted to the illustrated and described embodiments, since a number of variations are conceivable within the scope of the following Claims. For instance, as depicted in FIG. 11, the article may include a casing layer which is additional to casings layers 1 and 2, such as a second liquid-permeable casing layer 40 placed between the absorbent pad and that casing layer from which the fold is formed. Parts of this additional casing layer may also be included in the folds created, so as to provide a stronger fold having double inner and double outer sidewalls.

The variant in which two liquid-permeable casing layers are provided is particularly suitable when the folds in the longitudinal direction shall not extend over the whole of the article. In this case, the double casing layer is used solely in the crotch part, where it is most useful, and the end parts of the folds are fastened to the front and back part of the article in spaced relationship with the corresponding end edges. Instead of forming folds in the liquid-permeable casing layer, it is, of course, conceivable to instead form the folds in separate material layers which are placed on top of the casing layer of the article and which have no appreciable lateral extension beyond the fold lines, or at least do not extend right out to the side edges of the article. These separate material layers may either form one single discrete fold of limited extension also inwardly of the fold lines, or form two mutually spaced folds at respective side edges of the layer.

It will be also understood that inventive longitudinally and transversely extending folds can be combined, thus providing barriers around all edges of the article which fully circumvent a liquid and excrement receiving area inwardly of the folds.

It is also possible to place the common base line of the fold outwardly of the side edge or end edge of the absorbent pad, over the full length of the fold or over parts thereof.

We claim:

1. An absorbent article intended for one-time use only and comprising:
    a liquid-permeable upper casing layer intended to face towards a wearer in use;
    a lower casing layer intended to lie distal from the wearer in use;
    an absorbent pad sandwiched between said liquid-permeable upper casing layer and said lower casing layer;
    said article extending in a longitudinal direction and having one side edge and an opposite second side edge, said article further comprising a central receiving zone extending in said longitudinal direction and having a first edge and an opposite second edge spaced from said one and said second side edges, respectively, said first edge and said opposite second edge extending in said longitudinal direction;
    a first tubular fold arranged between said first edge and said one side edge, and a second tubular fold arranged between said opposite second edge and said opposite second side edge, each tubular fold comprised of a flexible material which extends in the longitudinal direction on a side of the article which is intended to face the wearer in use, so as to form leakage barriers;
    each fold having a first end part, a second end part, an intermediate part, and two first fold lines extending in the longitudinal direction, said first fold lines being close to one another so as to essentially coincide to form a common base line extending in the longitudinal direction;
    each fold extending in a lateral direction away from the base line in opposite directions;
    two elastic elements mounted within each tubular fold in a pre-stretched state and along said fold with one elastic element positioned on each side of the base line;
    said first and second end parts having a maximum extension in said lateral direction and terminating at second fold lines on each side of said base line, said two elastic elements respectively extending along said second fold lines;
    said end parts being joined to the liquid-permeable upper casing layer in a flat state, the folds being sufficiently spaced apart to enable body fluids to collect therebetween;
    said two elastic elements being joined to the fold along said second fold lines only at the first and second end parts of the fold; and
    all portions of the intermediate part of the fold and the two elastic elements extending therethrough being freely movable, whereby in an extended flat state of the article, each tubular fold including the intermediate part is flat, with each of the two elastic elements located on a respective side of the base line, and when in use, the article is forcibly curved to conform to a body of the wearer, and the intermediate part of each fold will lift vertically as a result of the action of the two elastic elements, so as to form said leakage barriers.

2. An article according to claim 1, wherein the base line of the folds are located inwardly of side edges of the absorbent pad, respectively.

3. An article according to claim 1, wherein each fold extends laterally equidistant from its base line in both directions, at least at one end part of the fold.

4. An article according to claim 1, wherein each fold extends laterally to different extents in respective direction from its base line, at least at one end part of the fold.

5. An article according to claim 1, further flexible material of each fold is the liquid-permeable upper casing layer.

6. An article according to claim 5, further including a separate causing layer beneath each fold and joined thereto on both sides of each fold's baseline to strengthen each fold.

7. An article according to claim 1, wherein the article is a diaper and includes additional elastic elements placed inside flaps which includes part of the upper and the lower casing layer and which extend laterally beyond side edges of the absorbent pad, and said additional elastic elements functioning as legs elastication when the diaper is in use.

8. An absorbent article intended for one-time use only and comprising:

a liquid-permeable upper casing layer intended to face towards a wearer in use;

a lower casing layer intended to lie distal from the wearer in use;

an absorbent pad sandwich between said liquid-permeable upper casing layer and said lower causing layer;

said article extending in a longitudinal direction and having two side edges, a first end edge and an opposite second end edge, a front part intended to lie forwardly of the wearer in use, a back part intended to lie rearwardly of the wearer in use, and a crotch part located between said front and said back parts said article further comprising a central receiving zone extending in said longitudinal direction and having a first edge and an opposite second edge spaced from said first and said opposite second end edges, respectively, said first edge and said second opposite second edge extending in a direction transverse to said longitudinal direction;

a first tubular fold arranged between said first edge and said first end edge, and a second tubular fold arranged between said opposite second edge and said opposite second end edge, each tubular fold comprised of a flexible material which extends in the transverse direction on a side of the article which is intended to face the wearer in use, so as to form leakage barriers;

each fold having a first end part, a second end part, an intermediate part, and two first fold lines extending in the transverse direction, said first fold lines being close to one another so as to essentially coincide to form a common base line extending in the tranverse direction;

each fold extending in said longitudinal direction away from the base line in opposite directions;

two elastic elements mounted within each tubular fold in a pre-stretched state and along said fold with one elastic element positioned on each side of the base line;

said first and second end parts having a maximum extension in the longitudinal direction and terminating at second fold lines on each side of said base line, said two elastic elements, respectively, extending along said second fold lines;

said end parts being joined to the liquid-permeable upper casing layer in a flat state, the folds being sufficiently spaced apart to enable body fluids to collect therebetween;

said two elastic elements being joined to the fold along said second fold lines only at the first and second end parts of the fold; and all portions of the intermediate part of the fold and the two elastic elements extending therethrough being freely movable, whereby in an extended flat state of the article, each tubular fold including the intermediate part is flat, with each of the two elastic elements located on a respective side of the base line, and when in use, the article is forcibly curved to conform to a body of the wearer, and the intermediate part of each fold will lift vertically as a result of the action of the two elastic elements, so as to form said leakage barriers.

9. An article according to claim 8, wherein said first and second folds are located close to said first and second end edges, respectively, of the article.

10. An article according to claim 8, wherein each fold extends longitudinally to different extents in respective directions from its base line, at least at one end part of the fold.

11. An article according to claim 8, wherein each fold extends longitudinally equidistant from its base line in both directions, at least at one end part of the fold.

12. An article according to claim 8, wherein the flexible material of each fold is the liquid-permeable upper casing layer.

13. An article according to claim 8, further including a separate casing layer beneath each fold and joined thereto on both sides of each fold's base line to strengthen each fold.

* * * * *